United States Patent
Albers et al.

(10) Patent No.: US 6,723,333 B1
(45) Date of Patent: Apr. 20, 2004

(54) MOULDED BODIES MADE OF THERMOPLASTIC POLYURETHANE CONTAINING AN ACTIVE SUBSTANCE

(75) Inventors: Reinhard Albers, Leverkusen (DE); Ralf Dujardin, Willich (DE); Heinz Pudleiner, Krefeld (DE); Joachim Simon, Düsseldorf (DE); Günther Eberz, Odenthal-Holz (DE); Wolfgang Kreiss, Bergisch Gladbach (DE); Christina Krasemann-Sharma, Hilden (DE)

(73) Assignee: Bayer Aktiengesellschaft, Leverkusen (DE)

( * ) Notice: Subject to any disclaimer, the term of this patent is extended or adjusted under 35 U.S.C. 154(b) by 557 days.

(21) Appl. No.: 09/646,339
(22) PCT Filed: Mar. 10, 1999
(86) PCT No.: PCT/EP99/01536
§ 371 (c)(1), (2), (4) Date: Sep. 15, 2000
(87) PCT Pub. No.: WO99/48542
PCT Pub. Date: Sep. 30, 1999

(30) Foreign Application Priority Data

Mar. 20, 1998 (DE) .......................... 198 12 160

(51) Int. Cl.$^7$ ............................... A61L 29/00
(52) U.S. Cl. .................. 424/422; 424/423; 424/426
(58) Field of Search ......................... 424/422, 423, 424/426

(56) References Cited

U.S. PATENT DOCUMENTS

| 5,019,096 A | 5/1991 | Fox, Jr. et al. ................ 623/1 |
| 5,616,338 A | 4/1997 | Fox, Jr. et al. ............. 424/423 |
| 5,624,704 A * | 4/1997 | Darouiche et al. ......... 427/2.24 |
| 5,707,366 A * | 1/1998 | Solomon et al. ............ 604/256 |

FOREIGN PATENT DOCUMENTS

| DE | 4143239 | 7/1993 |
| EP | 0 596 615 | 5/1994 |
| WO | 96/22114 | 7/1996 |
| WO | WO-96/22114 A1 * | 7/1996 |

\* cited by examiner

Primary Examiner—Thurman K. Page
Assistant Examiner—Rachel M. Bennett
(74) Attorney, Agent, or Firm—Joseph C. Gil; Aron Preis; James R. Franks

(57) ABSTRACT

The invention provides moulded items made from thermoplastic polyurethanes (TPUs), in particular medical articles such as central venous catheters which contain a homogeneous distribution of antibiotic substances, a process for the preparation thereof and preparation of the active substance-containing TPUs.

4 Claims, 1 Drawing Sheet

MOULDED BODIES MADE OF THERMOPLASTIC POLYURETHANE CONTAINING AN ACTIVE SUBSTANCE

Figure 1:
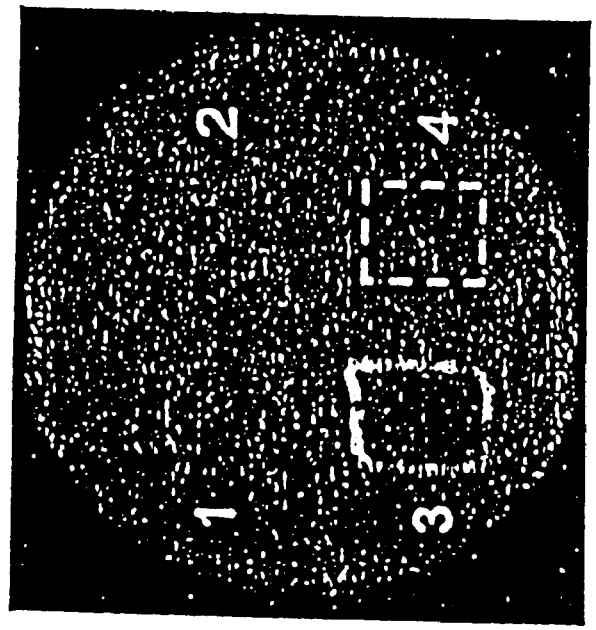
Figure 1:
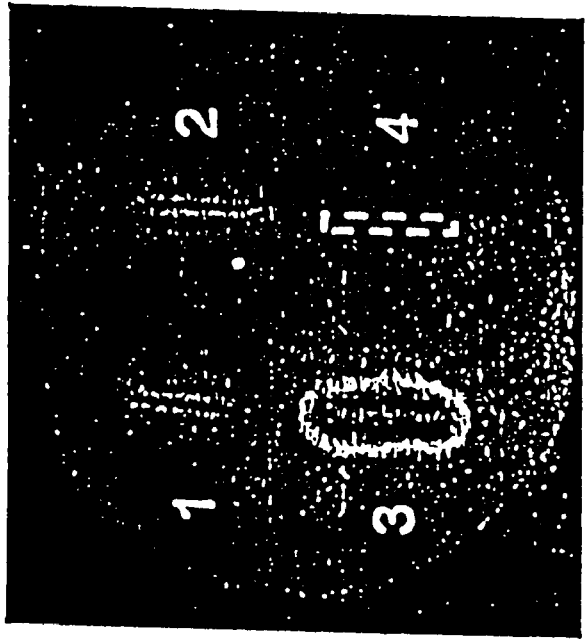

This application is a 371 of PCT /EP99/01536 filed May 10, 1999.

The invention provides moulded items made from thermoplastic polyurethanes (TPUs), in particular medical articles such as central venous catheters which contain a homogeneous distribution of antibiotic substances, a process for the preparation thereof and preparation of the active substance-containing TPUs.

The use of polymer materials for diagnostic and therapeutic purposes has led to a significant technological advance in modem medicine. On the other hand the frequent use of these materials in medicine has led to a dramatic increase in so-called foreign body infections/polymer associated infections.

In addition to traumatic and thromboembolic complications, catheter-associated infections right up to sepsis represent serious problems when using central venous catheters in intensive medicine.

Numerous studies have shown that coagulase-negative Stapphylococci, the transient bacterium *Staphylococcus aureus* and various species of Candida are the main causes of catheter-associated infections. These microorganisms, which are always present on the skin, penetrate the physiological skin barrier when using the catheter and thus gain access to the subcutaneous region and ultimately the bloodstream. The adhesion of bacteria to the surface of the plastic material is thought to be the essential step for pathogenesis of foreign body infections. After adhesion of the skin bacteria to the polymer surface, the metabolically active proliferation of bacteria starts with colonisation of the polymer. This is accompanied by the production of a biofilm due to the bacterial excretion of extracellular glyclocalyx. The biofilm encourages adhesion of the pathogen and protects it from attack by specific cells in the immune system. In addition, the film forms a barrier which is impenetrable to many antibiotics. Following increased proliferation of the pathogenic bacteria on the surface of the polymer, septic bacteraemia may finally occur. Removal of the infected catheter is required in order to treat these types of infections since chemotherapy with antibiotics would require large, physiologically unacceptable, doses.

The frequency of bacterially induced infections involving central venous catheters is on average about 5%. Overall, central venous catheters are responsible for about 90% of all cases of sepsis in intensive medicine. The use of central venous catheters therefore not only involves a high risk of infection for patients but also causes very high secondary treatment costs (post-treatment, extended residence times in hospital).

These problems can only partly be solved by pre-, perior post-operative measures (e.g. hygiene precautions, etc.). A sensible strategy for preventing polymer-associated infections comprises modifying the polymer materials used. The objective of this modification must be the inhibition of bacterial adhesion and proliferation of bacteria which are already adhering, in order to avoid causal foreign body infections. This can be achieved by incorporating a suitable chemical substance in the polymer matrix (e.g. antibiotics), provided that the active substance incorporated can also diffuse out of the polymer matrix. In this case, release of the antibiotic can be extended over a relatively long period, which means that bacterial adhesion and proliferation on the polymer can be prevented for a correspondingly long period.

Methods for preparing antibacterial polymers for medical applications are already known. In the many processes described, addition of the active substance takes place using the following techniques:
a) Adsorption on the polymer surface (passively or via surfactants)
b) Introduction in a polymer coating which is applied to the surface of a moulded item
c) Incorporation in the bulk phase of the polymeric carrier substance
d) Covalent bonding to the polymer surface.

DE-A-41 43 239, for example, describes a process for introducing active substances into the outer layer of medical articles (impregnation). In this case, the implantable device made of a polymer material is steeped in a suitable solvent. The polymer matrix then becomes modified so that a pharmaceutically active substance or combination of active substances can penetrate into the polymer material of the implant. After removing the solvent, the active substance is embedded in the polymer matrix. After contact with the physiological medium, the active substance contained in the implantable device is released again by diffusion. The release profile can be adjusted by the choice of solvent and by varying the experimental conditions.

Polymer materials for medical applications which have active substance-containing coatings are mentioned, for example, in EP-A 328 421. Processes for preparing antimicrobially active coatings and methods of applying to the surfaces of medical devices are described. The coatings consist of a polymer matrix, in particular made of polyurethanes, silicones or biodegradable polymers, and an antimicrobial substance, preferably a synergistic combination of a silver salt and chlorhexidine or an antibiotic.

A common feature of all the processes mentioned is the fact that providing the medical working device with an antibiotic substance requires an additional working step, that is either pretreatment of the polymer material prior to processing or post-treatment of the moulded item when produced. This results in additional costs and involves extra time during production. Another problem associated with the processes is the use of organic solvents, most of which cannot be completely removed from the material.

The object of the invention was to provide moulded items with an antibiotic action, in particular medical articles such as catheters, which effectively prevent surface colonisation by bacteria for a relatively long period (2–4 weeks).

It has now been found that this can be achieved when moulded items are used which release a concentration of an antibiotic substance at the surface which can stop colonisation by bacteria for a relatively long period and which have a low surface roughness.

Thus, the object of the invention is moulded items made from thermoplastic polyurethanes which contain a homogeneous distribution of an antibiotic substance and which have a peak-to-valley surface roughness of <5 $\mu$m, preferably <2 $\mu$m, in particular <1 $\mu$m.

The antibiotic substances may in principal be any active substances which have a wide range of action against the pathogenic microorganisms involved in polymer-associated infections, in particular against coagulase-negative Staphylococci, *Staphylococcus aureus* and species of Candida. According to the invention, the antibiotic substances may also be used as active substance combinations in the moulded items, provided their effects are not antagonistic.

The active substances used must have sufficient (chemical) stability in the polymer matrix. In addition, the microbiological activity of the active substance should not be impaired in the polymer matrix and under the process conditions prevailing during incorporation; the active substance must therefore be sufficiently stable at the temperatures required for thermoplastic processing of the polymer material, 150 to 200° C., with residence times of 2 to 5 minutes.

Incorporation of the pharmaceutically active substance should not impair either the biocompatibility of the polymer surface or other desirable polymer-specific properties of the polymer material (elasticity, tear strength, etc.).

Suitable antibiotic substances are, for example, nalidixic acid and derivatives of nalidixic acid such as, for example, ciprofloxacin, norfloxacin, ofloxacin, pefloxacin, enoxacin, preferably ciprofloxacin, aminoglycosides such as, for example, gentamycin, kanamycin, amikacin, sisomycin, preferably gentamicin and kanamycin, macrocyclic antibiotics such as, for example, rifampicin or erythromycin, preferably rifampicin, bacitracin, mupirocin, thyrothricins such as, for example, gramicidin, tyrocidin, lincomycin, clindamycin or fusidic acid.

The active substances are preferably incorporated at a concentration corresponding to their antibiotic activity. The active substances are particularly preferably used in the concentration range 0.1 to 5.0 wt. %.

The thermoplastically processable polyurethanes which can be used according to the invention are obtainable by reaction of the polyurethane-forming components
A) organic diisocyanate,
B) linear hydroxyl-terminated polyol with a molecular weight of 500 to 10000,
C) chain-extender with a molecular weight of 60 to 500,
wherein the molar ratio of NCO groups in A) to groups which can react with isocyanate in B) and C) is 0.9 to 1.2.

Suitable diisocyanates A) are, for example, aliphatic, cycloaliphatic, heterocyclic and aromatic diisocyanates such as are described in Justus Liebigs Annalen der Chemie, 562, p. 75–136. Aliphatic and cycloaliphatic diisocyanates are preferred.

The following may be mentioned in detail: aliphatic diisocyanates such as hexamethylene diisocyanate, cycloaliphatic diisocyanates such as isophorone diisocyanate, 1,4-cyclohexane diisocyanate, 1-methyl-2,4-cyclohexane diisocyanate and 1-methyl-2,6-cyclohexane diisocyanate and also corresponding mixtures of isomers, 4,4'-dicyclohexylmethane diisocyanate, 2,4'-dicyclohexylmethane diisocyanate and 2,2'-dicyclohexylmethane diisocyanate and corresponding mixtures of isomers, aromatic diisocyanates such as 2,4-toluylene diisocyanate, mixtures of 2,4-toluylene diisocyanate and 2,6-toluylene diisocyanate, 4,4'-diphenylmethane diisocyanate, 2,4'-diphenylmethane diisocyanate, and 2,2'-diphenylmethane diisocyanate, mixtures of 2,4'-diphenylmethane diisocyanate and 4,4'-diphenylmethane diisocyanate, urethane-modified liquid 4,4'-diphenylmethane diisocyanate and 2,4'-diphenylmethane diisocyanate, 4,4'-diisocyanatodiphenylethane-1,2 and 1,5-naphthylene diisocyanate. 1,6-hexamethylene diisocyanate, isophorone diisocyanate, dicyclohexylmethane diisocyanate, isomeric mixtures of diphenylmethane diisocyanates with a 4,4'-diphenylmethane diisocyanate concentration of >96 wt. % are preferably used and in particular 4,4'-diphenylmethane diisocyanate and 1,5-naphthylene diisocyanate. The diisocyanates mentioned may be used individually or in the form of mixtures with each other. They may also be used together with up to 15 wt. % (calculated on the basis of the total amount of diisocyanate) of a polyisocyanate, for example triphenylmethane-4,4'-4''-triisocyanate or polyphenyl-polymethylene-polyisocyanates.

Linear hydroxyl-terminated polyols with an average molecular weight $M_n$ of 500 to 10000, preferably 500 to 5000, particularly preferably 600 to 2000, are used as component B). As a result of the method of production, these often contain small amounts of branched compounds. Frequently, therefore, these are also called "substantially linear polyols". Polyetherdiols, polycarbonatediols, sterically hindered polyesterdiols, hydroxyl-terminated polybutadienes or mixtures of these are preferred.

As plasticising segments, polysiloxanes of the formula (I)

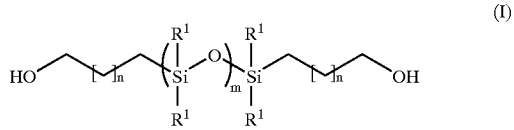

(I)

wherein
m has a value of 1 to 30, preferably 10 to 25 and particularly preferably 15 to 25,
n has a value of 1 to 4 and
$R^1$ is an alkyl group with 1 to 6 carbon atoms or a phenyl group,
may also be used, on their own or mixed with the diols mentioned above. These are known products and may be prepared by methods of synthesis which are known per se, for example by reacting a silane of the formula (II)

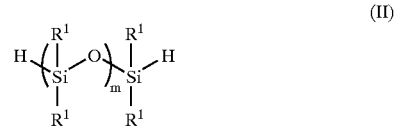

(II)

in the ratio 1:2 with an unsaturated, aliphatic or cycloaliphatic alcohol such as allyl alcohol, buten-1-ol or penten-1-ol in the presence of a catalyst, e.g. hexachloroplatinic acid.

Suitable polyetherdiols may be prepared by reacting one or more alkylene oxides with 2 to 4 carbon atoms in the alkylene groups with a starter molecule which contains two active, bonded hydrogen atoms. The following may be mentioned as alkylene oxides, for example: ethylene oxide, 1,2-propylene oxide, epichlorhydrin and 1,2-butylene oxide and 2,3-butylene oxide. Ethylene oxide, propylene oxide and mixtures of 1,2-propylene oxide and ethylene oxide are preferably used. The alkylene oxides may be used individually, alternating with each other or as mixtures. The following are suitable as starter molecules, for example: water, aminoalcohols such as N-alkyl-diethanolamines, for example N-methyl-diethanolamine, and diols such as ethylene glycol, 1,3-propylene glycol, 1,4-butanediol and 1,6-hexanediol. Optionally, mixtures of starter molecules may also be used. Suitable polyetherdiols are also the hydroxyl group-containing polymerisation products of tetrahydrofuran. Trifunctional polyethers may be used in proportions of 0 to 30 wt. %, with respect to the bifunctional polyethers, but at most in amounts such that a thermoplastically processable product is obtained. The substantially linear polyetherdiols may be used either individually or in the form of mixtures with each other.

Suitable sterically hindered polyesterdiols may be prepared, for example, from dicarboxylic acids with 2 to 12 carbon atoms, preferably 4 to 6 carbon atoms, and polyhydric alcohols. Suitable dicarboxylic acids are, for example: aliphatic dicarboxylic acids such as succinic acid, glutaric acid, adipic acid, suberic acid, azelaic acid and sebacic acid and aromatic dicarboxylic acids such as phthalic acid, isophthalic acid and terephthalic acid. The dicarboxylic acids may be used individually or as mixtures, e.g. in the form of a succinic, glutaric and adipic acid mixture. To prepare the polyesterdiols, it may optionally be advantageous to use the corresponding dicarboxylic acid derivatives instead of the dicarboxylic acids, such as diesters of the carboxylic acids with 1 to 4 carbon atoms in the alcohol group, or the anhydrides or acid chlorides of the carboxylic acids. Examples of polyhydric alcohols are sterically hindered glycols with 2 to 10, preferably 2 to 6, carbon atoms which have at least one alkyl group in the β-position with respect to the hydroxyl group, such as 2,2-dimethyl-1,3-propanediol, 2-methyl-2-propyl-1,3-propanediol, 2,2-diethyl-1,3-propanediol, 2-ethyl-1,3-hexanediol, 2,5-dimethyl-2,5-hexanediol, 2,2,4-trimethyl-1,3-propanediol or mixtures with ethylene glycol, diethylene glycol, 1,4-butanediol, 1,5-pentanediol, 1,6-hexanediol, 1,10-decanediol, 1,3-propanediol and dipropylene glycol. Depending on the properties required, the polyhydric alcohols may be used individually or optionally as mixtures with each other. Esters of carbonic acid with the diols mentioned, in particular those with 3 to 6 carbon atoms such as 2,2-dimethyl-1,3-propanediol or 1,6-hexanediol, condensation products of hydroxycarboxylic acids, for example hydroxycaproic acid, and polymerisation products of lactones, for example optionally substituted caprolactones, are also suitable. Neopentylglycol-polyadipate, 1,6-hexanediol-neopentylglycol-polyadipate are preferably used as polyesterdiols. The polyesterdiols may be used individually or in the form of mixtures with each other.

Diols, diamines or aminoalcohols with a molecular weight of 60 to 500 are used as chain extenders C), preferably aliphatic diols with 2 to 14 carbon atoms such as, for example, ethanediol, 1,6-hexanediol, diethylene glycol, dipropylene glycol and in particular 1,4-butanediol. However, diesters of terephthalic acid with glycols with 2 to 4 carbon atoms, such as, for example, bis-ethyleneglycol terephthalate, bis-1,4-butanediol terephthalate, hydroxyalkylene ethers of hydroquinone such as, for example, 1,4-di-(hydroxyethyl)-hydroquinone, ethoxylated bisphenols, (cyclo)aliphatic diamines such as, e.g. isophorone diamine, ethylene diamine, 1,2-propylene diamine, 1,3-propylene diamine, N-methyl-propylene-1,3-diamine, 1,6-hexamethylene diamine, 1,4-diaminocyclohexane, 1,3-diaminocyclohexane, N,N'-dimethyl-ethylene diamine and 4,4'-dicyclohexylmethane diamine and aromatic diamines such as e.g. 2,4-toluylene diamine and 2,6-toluylene diamine, 3,5-diethyl-2,4-toluylene diamine and 3,5-diethyl-2,6-toluylene diamine and primary mono-, di-, tri- or tetraalkyl substituted 4,4'-diaminodiphenylmethanes or aminoalcohols such as ethanolamine, 1-aminopropanol, 2-aminopropanol, are also suitable. Mixtures of the chain extenders mentioned above may also be used. In addition, small amounts of trifunctional and higher functional cross-linking agents may be added, e.g. glycerol, trimethylolpropane, pentaerythritol, sorbitol. 1,4-butandiol, 1,6-hexanediol, isophorone diamine and mixtures of these are particularly preferred.

Furthermore, conventional monofunctional compounds may also be used in small amounts, e.g. as chain terminators or mould release aids. Alcohols such as octanol and stearyl alcohol or amines such as butylamine and stearylamine may be mentioned by way of example.

The molar ratio of the structural components may be varied between wide limits, which enables adjustment of the properties of the product. Molar ratios of polyols to chain extenders of 1:1 to 1:12 have proven useful. The molar ratio of diisocyanates to polyols is preferably 1.2:1 to 30:1. Ratios of 2:1 to 12:1 are particularly preferred. To prepare the TPUs, the structural components, optionally in the presence of catalysts, auxiliary substances and additives, are reacted in amounts such that the ratio by equivalents of NCO groups to the sum of the NCO-reactive groups, in particular the hydroxy or arnino groups in the low molecular weight diols/triols, arnines and polyols, is 0.9:1 to 1.2:1, preferably 0.98:1 to 1.05:1, particularly preferably 1.005:1 to 1.01:1.

Polyurethanes which can be used according to the invention may be prepared without catalysts; in many cases, however, the use of catalysts may be indicated. In general, the catalysts are used in amounts of up to 100 ppm, with respect to the total amount of reactants. Suitable catalysts according to the invention are the conventional tertiary amines known per se from the prior art such as, for example, triethylamine, dimethylcyclohexylamine, N-methylmorpholine, N,N'-dimethylpiperazine, 2-(dimethyl-amino-ethoxy)-ethanol, diazabicyclo-[2.2.2]-octane and similar compounds and also in particular organic metal compounds such as esters of titanic acid, iron compounds, tin compounds, e.g. tin diacetate, tin dioctoate, tin dilaurate or the tindialkyl salts of aliphatic carboxylic acids. Dibutyltin diacetate and dibutyltin dilaurate are preferred; amounts of 1 to 10 ppm of these are sufficient to catalyse the reaction.

Other auxiliary substances and additives may also be added in addition to the TPU components and catalysts. The following may be mentioned, for example: lubricants such as fatty acids, metal soaps of these, fatty acid amides and silicone compounds, antiblocking agents, inhibitors, hydrolysis, light, heat and discoloration stabilisers, flame retardants, colorants, pigments, inorganic or organic fillers and reinforcing agents. Reinforcing agents are in particular fibrous reinforcing substances such as inorganic fibres which are prepared according to the prior art and may also be provided with a size dressing. More detailed data relating to the auxiliary substances and additives can be found in the specialist literature, for example J.H. Saunders, K.C. Frisch: "High Polymers", vol. XVI, Polyurethanes, parts 1 and 2, Interscience Publishers 1962 and 1964, R. Gäichter, H. M üller (eds.): Taschenbuch der Kunststoff-Additive, 3rd edition, Hanser Verlag, Munich 1989, or DE-A 29 01 774.

Building up the thermoplastically processable polyurethane elastomers is preferably performed stepwise in a so-called prepolymer process. In a prepolymer process, an isocyanate-containing prepolymer is formed from the polyol and the diisocyanate and this is reacted with the chain extender in a second step. The TPUs may be prepared continuously or batchwise. The best-known industrial methods of preparation are the belt process and the extruder process.

Systematic investigations have shown that homogeneous distribution of the pharmaceutically active substance in the polymer matrix is required in order to be able to use active substance diffusion as an adjustable release mechanism. The antibiotic substance and the polymer carrier substance used should therefore be highly physico-chemically compatible. One measure of the compatibility of active substance and matrix is the interfacial energy appearing in the system. If this is large, then the active substance and matrix are not very compatible and the active substance is eliminated rapidly; the concentration of active substance at the polymer surface falls below the activity threshold within a short time. If the interfacial energy is very low, the active substance is strongly bonded by the polymer matrix; release of an effective amount at the surface does not occur. In the event of good physico-chemical compatibility between the active substance and the matrix a high diffusion coefficient is produced for active substance in the polymer. The level for the rate of release of antibiotic substance can be regulated in this case by varying the amount of active substance incorporated, since the amount of active substance released is then proportional to the concentration of active substance in the matrix.

To prepare moulded items according to the invention, combinations of matrix and active substance which have an interfacial energy of preferably 3 to 30 mN/m, particularly preferably 8 to 15 mN/m, very particularly preferably 10 to 13 mN/m are chosen. A preferred combination according to the invention is ciprofloxacin in a matrix of a TPU prepared from polytetrahydrofuran, isophorone diisocyanate, isophorone diamine and 1,6-hexanediol, which is sold under the tradename Texin® 5590 (Bayer Corp., Pittsburgh, Pa. 15205-9741). Active substance concentrations between 0.1 and 1.0 wt. % of ciprofloxacin are sufficient to effectively prevent bacterial surface colonisation of the polymer surface. In-vivo and in-vitro experiments have shown that catheters according to the invention, made from ciprofloxacin-containing Texin® 5590, bring about a reduction in bacterial colonisation of up to 75% over a period of 7 days, as compared with active substance-free reference material.

Moulded items according to the invention are characterised in that they have a molecular disperse distribution of the antibiotic substance in the polymer matrix. The high morphological homogeneity of the extruded active substance-containing plastic material can be demonstrated by means of visible light microscope and scanning electron microscope images. In addition, it can be demonstrated, using scanning electron microscope images, that the polymer has a smooth surface before and after release of the incorporated active substance, i.e. the biocompatibility of the polymer surface is not impaired by the addition or by the release of the active substance. The surface of moulded items according to the invention has a peak-to-valley surface roughness of <5 µm, preferably <2µm, particularly preferably <1 µm. This is an essential factor for good biocompatibility of moulded items according to the invention and also hinders colonisation by bacteria and adherence of cellular blood constituents on the surface.

In contrast, comparable active substance-containing samples which have been prepared by the solvent casting process are much more inhomogeneous. Scanning electron microscope tests show that some of the incorporated active substances are present in the form of crystal associations in the polymer matrix and on the surface. The crystal associations cause a drastic impairment in the mechanical properties of the polymer. In addition, leached out crystal associations leave a rough surface exposed which leads to reduced biocompatibility.

Furthermore, contrary to expectations, it was found that the mechanical properties of the polymer are markedly improved by the addition of an antibiotic substance in amounts of 0.01 to 10 wt. %, preferably 0.1 to 5 wt. %.

The incorporated active substance modifies the surface tension of the plastic phase of the TPU, formed substantially from component (B), thus increasing phase separation of the block copolymers, and thus improves the morphology of the polymer. As a result of the improved morphology, the incorporated active substances cause a clear improvement in mechanical properties, in addition to improved biocompatibility. Thus, the tensile strength of an active substance-containing TPU is significantly higher than that of the active substance-free TPU and the permanent strain is measurably reduced. The elongations at break are reduced only slightly, which also indicates an improved elastomer structure in the TPU.

Moulded items according to the invention can be prepared by extruding a melt consisting of the polymer and the active substance. The melt may contain 0.01 to 10 wt. %, preferably 0.1 to 5 wt. %, of active substance. Mixing the components may 5 be achieved in any way using known techniques. The active substance may, for example, be incorporated directly into the polymer melt in the solid form. An active substance-containing masterbatch may also be melted directly with the polymer or be mixed with the polymer already present as a melt. The active substance may also be applied to the polymer before melting the polymer using known techniques (rotating drum application, spraying, etc.).

Generally, the mixing/homogenisation of the components is performed using known techniques in compounding or screw machines, preferably in single or twin-screw extruders at temperatures in the range between 150 and 200° C.

A homogeneous, molecular disperse distribution of active substance in the polymer matrix is produced by mixing the components during the extrusion process, without additional working stages being required.

The active substance-containing granules obtained in this way can be further processed using the known techniques of thermoplastic processing (injection moulding, extrusion, etc). The moulded items are free from specks, flexible, non-tacky and can be sterilised with no problem using common methods.

EXAMPLES

Example 1 (comparison)

700 parts by wt. of Terathene® 2000 (DuPont) and 74.5 parts by wt. of 1,6-hexanediol were initially introduced into a flask with a ground glass joint, fitted with a stirrer and an internal thermometer, and dried at 110° C./20 mbar for 1 hour. Then 320.6 parts by wt. of isophorone diisocyanate were added and the reaction mixture was stirred at 120° C. until reaching the theoretical NCO-value of 3.5 wt. %. Then 11.8 parts by wt. of Höchst wax C (Hoechst AG) and 7.5 parts by wt. of di-n-butylamine were added. The prepolymer was dissolved in toluene and added dropwise, with stirring at room temperature, to a solution of 71.6 parts by wt. of isophorone diamine in 2456 parts by wt. of a mixture of toluene and isopropanol (70/30). A colourless, transparent and homogeneous solution was obtained. After removing the solvent at 65° C./15 mbar, colourless, transparent polymer sheets were obtained and these were reduced in size using a chopping machine. The chopped granules were then extruded and extrusion-granulated using a ZSK1 twin-shaft extruder. Colourless, clear and non-tacky cylindrical granules were obtained.

Some of the cylindrical granules were injection moulded to give specimen items for microbiological in-vitro tests and for determining the release profile of the incorporated active substance (control trial).

Another portion was extruded to give tubes with an internal diameter of 3 mm for microbiological in-vivo tests (animal model).

Example 2

700 parts by wt. of Terathene® 2000 (DuPont) and 74.5 parts by wt. of 1,6-hexanediol were initially introduced into a flask with a ground glass joint, fitted with a stirrer and an internal thermometer, and dried at 110° C./20 mbar for 1 hour. Then 320.6 parts by wt. of isophorone diisocyanate were added and the reaction mixture was stirred at 120° C. until reaching the theoretical NCO-value of 3.5 wt. %. Then 11.8 parts by wt. of Höchst wax C and 7.5 parts by wt. of di-n-butylamine were added. The prepolymer was dissolved in 616 parts by wt. of toluene and added dropwise, with stirring at room temperature, to a solution of 71.6 parts by wt. of isophorone diamine in 2456 parts by wt. of a mixture of toluene and isopropanol (70/30). Then 11.74 g of ciprofloxacin-betaine (1.0 wt. % with respect to the polymer material) were stirred into the mixture. A colourless, transparent and homogeneous solution was obtained. After removing the solvent at 65° C./15 mbar, colourless, transparent polymer sheets were obtained and these were reduced in size using a chopping machine. The chopped granules were then extruded and extrusion-granulated using a ZSK1 twin-shaft extruder. Colourless, clear and non-tacky cylindrical granules were obtained.

Some of the cylindrical granules were injection moulded to give specimen items (sheets) for microbiological in-vitro tests and for determining the release profile of the incorporated active substance.

Another portion of the cylindrical granules was extruded to give tubes with an internal diameter of mm for microbiological in-vivo tests (animal model).

Example 3 (comparison)

Commercially available aliphatic polyetherurethane: Tecoflexe® EG 85 A (Thermedics, Woburn Mass. 01888-1799).

Example 4

5 g of bacitracin were applied to 995 g of active substance-free Tecoflex® EG 85 A in an intensive mixer. The active substance-containing cylindrical granules were extruded in a ZSK1 twin-shaft extruder. A clear melt was obtained which produced colourless, clear cylindrical granules after cooling in a water/air bath and extrusion-granulation.

The granules were injection moulded to give specimen items (sheets) for microbiological in-vitro tests and for determining the release profile of the incorporated active substance.

Example 5

5 g of gramicidin were applied to 995 g of active substance-free Tecoflex® EG 85 A in an intensive mixer. The active substance-containing cylindrical granules were extruded in a ZSK1 twin-shaft extruder. A clear melt was obtained which produced colourless, clear cylindrical granules after cooling in a water/air bath and extrusion-granulation.

The granules were injection moulded to give specimen items (sheets) for microbiological in-vitro tests and for determining the release profile of the incorporated active substance.

Example 6

S2-tensile bars were punched out of the specimen sheets of materials prepared in examples 3 to 5 and the strength characteristics were determined in accordance with DIN 53 455. The tension set for the specimen was determined in a similar manner to that described in DIN 53 518.

The results of the tests are summarised in table 1. This shows that the active substance contained in the polymer clearly improves the mechanical properties.

TABLE 1

| Experimental value | Tecoflex ® EG 85 A (example 3) | Tecoflex ® EG 85 A + 0.5 wt. % bacitracin (example 4) | Tecoflex ® EG 85 A + 0.5 wt. % gramicidin (example 5) |
|---|---|---|---|
| Tensile strength | 20.3 MPa | 29.2 MPa | 25 MPa |
| Extension at break | 750% | 630% | 700% |
| Permanent strain at 200% extension | 29% | 25% | 27% |
| Permanent strain at 400% extension | 74% | 66% | 72% |

Example 7

To prepare an active substance-containing masterbatch, 749 g of active substance-free cylindrical granules of thermoplastic polyurethane (Texin® 5590 Bayer Corp.) were dissolved in chloroform and 27.16 g of ciprofloxacin-betaine were added thereto. The mixture was heated (about 70° C.) until a colourless, homogeneous solution was obtained. After removing the solvent at 65° C./15 mbar, colourless, slightly opaque polymer sheets were obtained which were reduced in size using a chopping machine.

The 3.5 wt. % strength masterbatch was mixed with 1664 g of active substance-free cylindrical granules and extruded on a ZSK1 twin-shaft extruder. A clear melt was obtained which produced colourless, clear cylindrical granules after cooling in a water/air bath and extrusion-granulation.

The granules were injection moulded to give specimen items (sheets) for microbiological in-vitro tests.

Example 8

10 g of ciprofloxacin-betaine were applied to 990 g of active substance-free cylindrical granules (from example 1). The active substance-containing cylindrical granules were extruded on a ZSK1 twin-shaft extruder. A clear melt was obtained which produced colourless, clear cylindrical granules after cooling in a water/air bath and extrusion-granulation.

The granules were injection moulded to give specimen items (sheets) for microbiological in-vitro tests and for determining the release profile of the incorporated active substance.

Example 9

The release profile of ciprofloxacin-containing polymer samples was determined by elution in Millipore water (0.1% $NaN_3$). In a typical experiment, 20 ml of Millipore water were added to 5 g of active substance-containing tubular segments of Texin® 5590 (length: about 1 cm) at 37° C. and stirred at a constant speed. The elution agent was replaced with fresh Millipore water at regular 24 hour intervals. Quantification of the ciprofloxacin released in the corresponding solutions was performed by HPLC analysis.

Release profiles were determined for different concentrations of incorporated active substance. Sample 1 contained no ciprofloxacin and was used as a negative control, sample 2 contained 0.1 wt. % and sample 3 contained 1.0 wt. % of ciprofloxacin. Results of the trials are summarised in table 2. This shows that the diffusion of active substance from the polymer can be used as an adjustable release mechanism: the higher the amount of active substance incorporated, the higher is the concentration of active substance released from the polymer matrix into the elution medium.

TABLE 2

Release profile for ciprofloxacin-containing tube samples, amount of ciprofloxacin released [mg/l]

| Time [h] | 0 | 24 | 48 | 72 | 91 | 168 | 192 | 216 | 240 |
|---|---|---|---|---|---|---|---|---|---|
| Sample 1 | 0 | 0 | 0 | 0 | 0 | 0 | 0 | 0 | 0 |
| Sample 2 | 0 | 1.01 | 1.61 | 2.22 | — | 2.95 | 3.59 | 4.21 | 4.85 |
| Sample 3 | 0 | 22.58 | 29.01 | 34.12 | 37.84 | 49.83 | 53.4 | 57.08 | 60.79 |

Example 10

Microbiological evaluation and quantification of the release of active substance was performed using a new bioimaging technique. This method makes use of the selective effect-dependent bioluminescence of sensor bacteria (*E. coli*—test strain), in order to render visible the biological activity of the released active substance. The gyrase-inhibiting effect of ciprofloxacin was used in the system according to the invention, Texin® 5590 ciprofloxacin.

For imaging of the antibacterial effect, about 1 cm² sized samples of the active substance-containing material were placed in a petri dish and covered with a suspension of sensor bacteria in agarose. After an incubation period of about 30 minutes, the effect-dependent bioluminescence was assessed using a video-imaging system (e.g. EG&G Berthold, Luminograph LB 980). Antibiotic samples then appeared as luminescing areas.

Using this method, it could be shown, inter alia, that the microbiological efficacy of the ciprofloxacin released from the polymer matrix was retained even after using the high temperatures of about 200° C. required for thermoplastic processing of polymers. In addition, local concentration differences (e.g. surface perturbations, freshly cut edges) were depicted by different strengths of intensity of luminescence. FIG. 1 shows bioluminescent images of ciprofloxacin-containing polymer specimens: samples 1 and 2 are ciprofloxacin-containing injection moulded films, sample 3 is a ciprofloxacin-containing cast film, sample 4 is an active substance-free polymer specimen (negative control). The left-hand picture in the figure shows the cross-section of the 1 cm² specimen sheets, the right-hand picture shows the samples from above. The luminescence images show that the cast film (3) released a higher dose of ciprofloxacin than the injection moulded films (1+2). The negative control (4), as expected, exhibited no luminescence.

Example 11

Evaluation of the microbiological in-vivo activity of ciprofloxacin-containing catheters was performed by qualitative comparison with active-substance-free control catheters in a pig model (KLOSTERHALFEN) developed at RWTH Aachen. In the model, pigs in which the immune system had been suppressed by infusion of sublethal doses of a lipopolysaccharide (LPS) were used. A stage corresponding to endotoxic shock in humans was intended to be produced in the experimental animal in this way.

For the test, a ciprofloxacin-containing test catheter and an active substance-free control catheter were implanted under sterile conditions in the right and left external jugular vein respectively of each of the experimental animals (n=10). After the passage of one week, the catheters were removed under sterile conditions, divided into 5 segments and tested microbiologically.

The results of the microbiological tests on the individual catheter segments can be summarised as follows:

Coagulase-negative staphylococci play the most important part during bacterial colonisation of the catheter.

Analysis of different catheter segments after an implantation period of 7 days demonstrate a descending, extraluminal bacterial colonisation with a maximum in the section of catheter which was at the subcutaneous level of the skin. The bacterial density and colonisation is progressively lower towards the tip of the catheter (see table 3).

Bacterial colonisation of the ciprofloxacin-containing test catheter is significantly lower than that of the active substance-free control catheter down to the region of the tip of the catheter (see table 3).

TABLE 3

Bacterial colonisation of different catheter segments after 7 days' implantation.
Statistical evaluation of 10 catheters per group (T-test).

| Group | Skin | Middle | $V_{prox}$ | $V_{dist}$ | Endol. |
|---|---|---|---|---|---|
| Controls | 99.8 ± 107.7 | 195 ± 139.7 | 7.7 ± 13.03 | 2.2 ± 6.9 | 0 ± 0 |
| Test | 5.9 ± 12.6 | 48.5 ± 71.6 | 0 ± 0 | 0.1 ± 0.32 | 0 ± 0 |
| p < | 0.014 | 0.009 | 0.078 | 0.353 | 0 | values cited in CFU, p=level of significance $v_{dist}$=tip of catheter, $v_{prox}$=5 cm, middle=10 cm, skin=15 cm

What is claimed is:

1. Moulded items made from a thermoplastically processable polyurethane containing a homogeneous distribution of an antibiotic substance which have a peak-to-valley surface roughness of <5 µm.

2. A process for preparing items according to claim 1 by extrusion or injection moulding of a thermoplastically processable polyurethane containing a homogeneous distribution of an antibiotic substance.

3. A process for preparing moulded items according to claim 1 by the mutual extrusion of an antibiotic substance and a thermoplastically processable polyurethane.

4. A medical article comprising the polyurethane of claim 1.

* * * * *